United States Patent [19]
Downey

[11] Patent Number: 5,304,340
[45] Date of Patent: Apr. 19, 1994

[54] METHOD OF INCREASING THE TENSILE STRENGTH OF A DILATATION BALLOON

[75] Inventor: Wolcott M. Downey, Melrose, Mass.

[73] Assignee: C. R. Bard, Inc., Murray Hill, N.J.

[21] Appl. No.: 43,409

[22] Filed: Apr. 6, 1993

Related U.S. Application Data

[63] Continuation of Ser. No. 755,696, Sep. 6, 1991, abandoned.

[51] Int. Cl.$^5$ .................... B29C 49/08; B29C 49/64
[52] U.S. Cl. .................... 264/521; 264/532; 264/570; 264/573; 604/96; 606/192; 606/194
[58] Field of Search ........... 264/521, 532, 570, 573; 604/96; 606/192, 194

[56] References Cited

U.S. PATENT DOCUMENTS

| | | | |
|---|---|---|---|
| 3,141,912 | 7/1964 | Goldman | 264/95 |
| 3,248,463 | 7/1966 | Wiley | 264/95 |
| 3,761,550 | 9/1973 | Seefluth | 264/25 |
| 3,786,221 | 1/1974 | Silverman | 219/10.57 |
| 3,787,170 | 1/1974 | Gilbert | 432/5 |
| 3,934,743 | 1/1976 | McChesney | 215/1 C |
| 4,044,086 | 8/1977 | McChesney | 264/97 |
| 4,235,837 | 11/1980 | Noonan | 264/520 |
| 4,490,421 | 12/1984 | Levy | 428/35 |
| 4,499,045 | 2/1985 | Obsomer | 264/532 |
| 4,522,779 | 6/1985 | Jabarin | 264/530 |
| 4,571,173 | 2/1986 | Chang | 432/9 |
| 4,820,349 | 4/1989 | Saab | 128/344 |
| 4,927,680 | 5/1990 | Collette | 428/36.92 |
| 4,935,190 | 6/1990 | Tennerstedt | 264/529 |
| 5,071,425 | 12/1991 | Gifford et al. | 264/573 |

FOREIGN PATENT DOCUMENTS

| | | |
|---|---|---|
| 0274411A2 | 7/1988 | European Pat. Off. . |
| 0439202A2 | 7/1991 | European Pat. Off. . |
| 0531117A3 | 3/1993 | European Pat. Off. . |
| 0531117A2 | 3/1993 | European Pat. Off. . |
| 57-117929 | 1/1981 | Japan .................. 264/521 |

OTHER PUBLICATIONS

Cakmak, Mukerrem; Dissertation. Dynamics and Structure Development in Biaxailly Stretched Polyethylene Terephthalate Films and Stretch Blow Molded Bottles, The University of Tennesse, 1984.

Hauenstein, J. D.; Morphology and Physical Properties of Polyester.

Heffelfinger, C. J.; A Survey of Film Processing Illustrated With Poly(Ethylene Terephthalate); Polymer Engineering and Science, vol. 18, No. 15, Nov. 1978.

*Primary Examiner*—Catherine Timm
*Attorney, Agent, or Firm*—Wolf, Greenfield & Sacks

[57] ABSTRACT

A method of making a dilatation balloon with a high percentage of the maximum tensile strength of the balloon material from a thin wall parison of a biaxially orientable polymer, such as polyethylene terephthalate (PET). A reverse temperature gradient (decreasing going from the inner to outer diameters) is applied across the sidewall of the parison by flowing a heated fluid through the parison and then sealing one end of the parison and expanding with a heated expansion fluid. Decreases in wall thickness and/or increases in burst strength across the wall can be achieved.

25 Claims, 3 Drawing Sheets

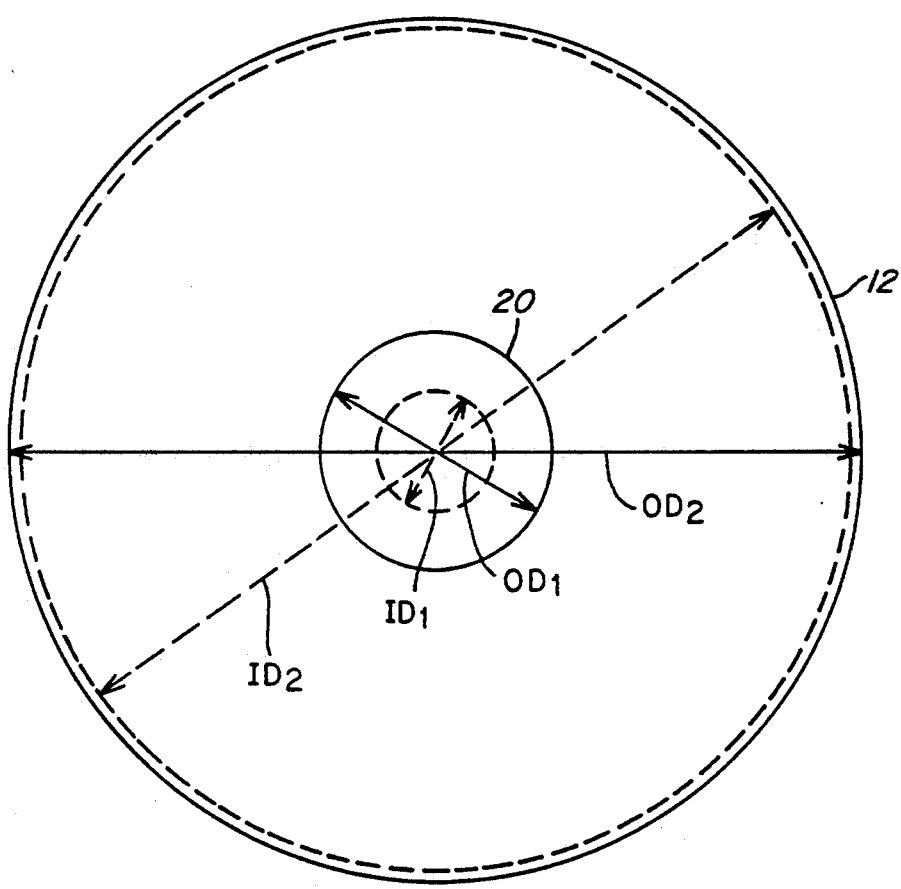

METHOD OF INCREASING THE TENSILE STRENGTH OF A DILATATION BALLOON

This application is a continuation of application Ser. No. 07/755,696, filed Sep. 6, 1991 now abandoned.

FIELD OF THE INVENTION

This invention relates to improvements in dilatation balloons used in medical procedures, and in particular to a method of increasing the tensile strength of a dilatation balloon.

BACKGROUND OF THE INVENTION

In a balloon dilatation procedure, a catheter carrying a balloon on its distal end is placed within a body cavity of a patient and is inflated to dilate the cavity. The procedure is commonly employed to dilate a stenosed artery, and in particular to dilate obstructed coronary arteries. Dilation procedures also are performed in peripheral blood vessels, the heart valves, and in other portions of the body.

There are several desirable features for a dilatation balloon. The balloon should have a maximum and controllable inflated diameter. Typically, a physician selects a balloon having an inflated diameter which corresponds to the inner diameter of the unobstructed blood vessel adjacent the stenosis to be treated—any expansion beyond this diameter may cause rupture of the vessel. The balloon should have a thin wall so that it can fold down closely about the catheter shaft to a low profile, thereby enabling the deflated balloon to be inserted into and removed from narrow stenoses and passageways. The balloon also needs to be flexible, as stiffness detracts from the ability of the balloon to bend as it is advanced through tortuous passageways, a characteristic sometimes referred to as "trackability." Low stiffness (high flexibility) also enables the balloon to be folded easily within the patient's body when the balloon is deflated. In this regard, it should be understood that when the balloon is deflated, it typically tends to collapse into a pair of wings which, if not sufficiently flexible, will not fold or wrap easily about the catheter body as the deflated balloon catheter is advanced or withdrawn against body tissue. The balloon should also have a sufficiently high burst strength to enable it to impart sufficient dilatation force to the vessel to be treated. However, the burst strength required for different procedures varies considerably because the dilating force of the balloon increases as a function of the diameter of the balloon, without requirinq a corresponding increase in the inflation pressure. Thus, the larger the diameter of the balloon, the lower its burst strength may be while still developing sufficient dilatation force. For example, a 20 millimeter (mm) diameter balloon used in a valvuloplasty procedure need only have a burst strength of about 3 to 6 atmospheres (atm), whereas a 3 mm diameter balloon used in the dilatation of small coronary arteries may require a burst pressure of 10 to 20 atm.

Dilatation balloons have been made from a variety of thermoplastic polymer materials, including polyesters, polyurethanes, polyvinyl chloride, thermoplastic rubbers, silicone polycarbonate copolymers, ethylene-vinyl acetate copolymers, ethylene butylene styrene block copolymers, polystyrene, acrylonitrile copolymers, polyethylene, polypropylene, and polytetrafluoro ethylene (PTFE). Each of these materials has different intrinsic properties and may require different processing techniques.

U.S. Pat. No. 4,490,421 to Levy (now Reissue 32,983) describes the processing of a semi-crystalline polyester homopolymer, namely, polyethylene terephthalate (PET), to produce a balloon having superior toughness, flexibility and tensile strength. The balloon is formed by heating a tubular parison in an external mold to a temperature above the orientation temperature, axially drawing and circumferentially expanding the parison to form a balloon and then cooling below the orientation temperature. To heat the parison above the orientation temperature, an external balloon mold is inserted into a heated liquid medium, or a heated liquid is passed through chambers in the mold, such that heat is applied to the exterior surface of the parison and time is allowed for the temperature across the parison sidewall to equilibrate. A relatively thin wall and high strength balloon is produced.

One of the problems with the known heating and expansion techniques for making PET balloons is that it produces a balloon having an optimum (high) tensile strength on the inner surface, but a much lower degree of strength on the outer surface. This varying degree of tensile strength across the sidewall results in a lower overall or "average" tensile strength. Ideally, it would be desirable to achieve the optimum (highest) tensile strength at both surfaces of the balloon and across the wall in order to achieve the highest average tensile strength.

The amount of orientation (and resulting strength) achieved at any point across the sidewall of a balloon made from a semi-crystalline orientable polymer (such as PET), is a function of temperature (higher temperature equals less orientation) and degree of stretch (higher stretch equals higher orientation). Thus, even if the inner and outer diameters of the parison start at the same temperature as intended with the prior art method, the orientation achieved at the inner diameter is greater due to the greater inherent degree of stretch at the inner surface. More specifically, due to the relative differences in thicknesses between the inner and outer diameters of the parison and balloon, the inner surface stretches more, and in most cases quite significantly more, and the degree of stretch is progressively less moving outwardly across the sidewall to the outer surface. Thus, while the inner surface may achieve the optimum (highest) tensile strength possible, the outer surface achieves a much lower degree of stretch and this reduces the overall o average tensile strength. Still further, if temperature equilibrium across the wall is not achieved and the outer surface of the balloon remains a higher temperature, then the inner surface is oriented to an even greater degree compared to the outer surface and the average tensile strength is even lower.

It is an object of this invention to increase the orientation at the outer surface and across the wall in order to provide a balloon having a higher average tensile strength.

It has been suggested in the art of making non-crystalline carbonated beverage bottles to provide a temperature gradient across the sidewall of the parison in order to prevent stress whitening (i.e., lack of clarity) and low impact strength which occur when the inner surface is stretched more than the outer surface. However, the bottle making method is not suitable for making a much thinner dilatation balloon and it was not known whether a temperature qradient could even be achieved in a very thin wall parison as used to make a dilatation balloon.

SUMMARY OF THE INVENTION

In accordance with this invention, a dilatation balloon is formed from a tubular, thin wall parison of an orientable polymer by subjecting the parison to a radially decreasing temperature gradient going from the inner to the outer diameter of the sidewall, in order to produce a substantially uniform and high degree of orientation across the sidewall and thus a higher average tensile strength. The temperature gradient is achieved in a thin wall parison by passing a heated fluid through a parison in a mold and then immediately drawing and expanding the parison while subject to said temperature gradient by sealing one end of the parison and injecting a heated fluid to expand the parison in the mold. Preferably, a semi-crystalline polymer is used such as polyethylene terephthalate. The processing parameters of inner and outer temperatures, and the degrees of inner and outer stretch, are selectively varied to produce a balloon dilatation catheter having an increased tensile strength and with either thinner walls or a higher burst strength.

BRIEF DESCRIPTION OF THE DRAWINGS

FIG. 3 is a diagram showing the relative inner and outer diameters of a starting parison and finished balloon for which the inner and outer stretch ratios are calculated.

DETAILED DESCRIPTION OF THE PREFERRED EMBODIMENT

Figure 1:
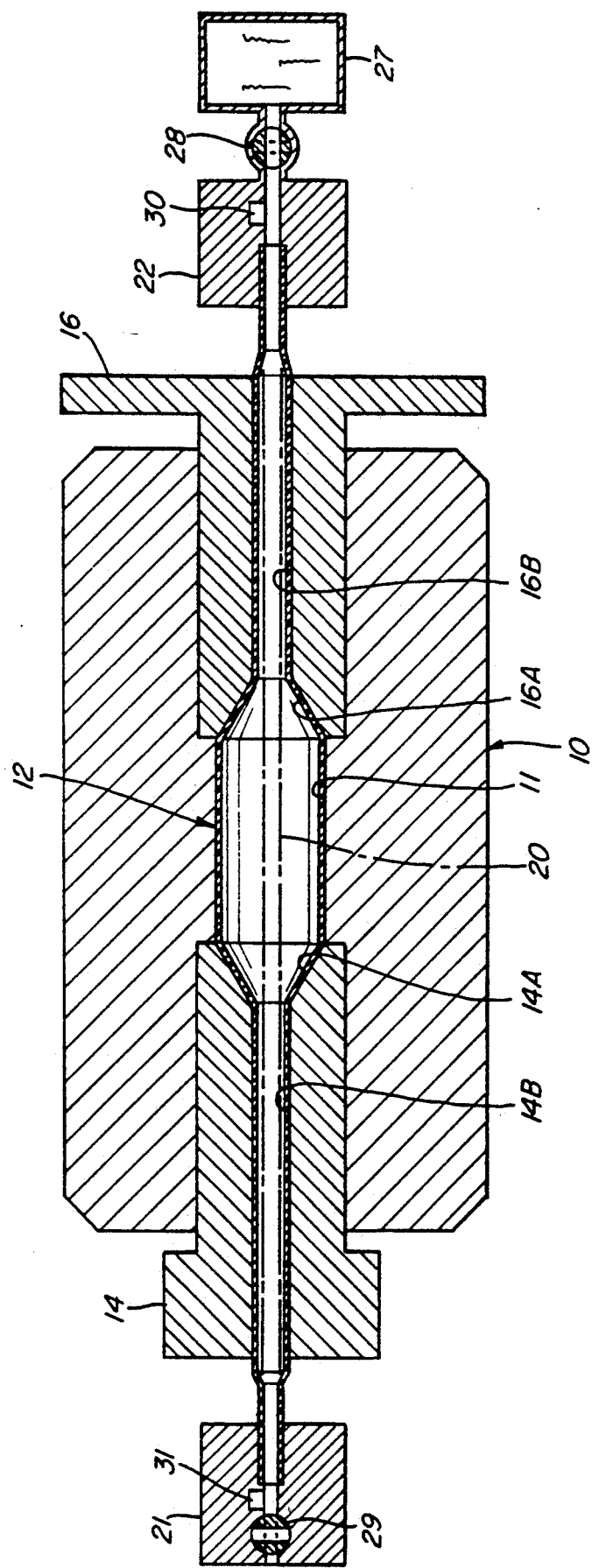
FIG. 1 is an illustration, in section, of a balloon-forming mold, showing a balloon within the mold, a tubular parison in phantom, and a source of heated fluid for passing through the parison.

A dilatation balloon 12 is formed in a mold as illustrated in FIG. 1. The mold includes a mold body 10 having a central internal bore 11, defining the intended outer diameter of the finished balloon 12, and a pair of end members, including a fixed end member 14 on the left and a movable end member 16 on the right. Both end members include outwardly tapering bore portions 14A, 16A, respectively, which merge into smaller diameter central end bores 14B, 16B, respectively.

The mold receives a tubular parison, indicated in phantom at 20 in FIG. 1. The parison 20 is gripped at its ends which extend outwardly of the mold, one of the ends being connected securely to an input fitting 22 connected to a source of heated fluid 27 under pressure via regulating valve 28, and the other end being connected securely to an output fitting 21 with a discharge valve or plug 29. In order to heat parison 20 above the orientation temperature and form a temperature gradient across the sidewall, a heated fluid from source 27 (such as a gas) flows from fitting 22 through the interior of the parison and exits fitting 21. The parison is then axially drawn by moving (means not shown) the end fittings 21 and 22 axially apart. The parison is then circumferentially expanded by closing valve 29 and injecting a heated expansion fluid (gas from source 27) into the parison from fitting 22; the axial drawing may also continue during expansion. Use of a heated expansion fluid acts to preserve the temperature gradient by preventing a cooling of the inner surface of the balloon, as occurs with an unheated expansion gas. It is preferred to use a heated gas both for heating the parison and expanding the same, such as hot nitrogen gas. The temperature at the entrance and exit of the parison is monitored by sensors 30, 31 in the fittings 22, 21 respectively.

The parison is preferably formed from an orientable semi crystalline polymer such as polyethylene terephthalate (PET). PET is an aromatic linear polyester derived from an aromatic dicarboxylic acid or its derivative as the main acid component, and an aliphatic glycol as the main glycol component. It can be melt extruded into a variety of formed structures. Typical examples of other aromatic dicarboxylic acid polymers that meet these criteria are derived from materials such as terephthalic acid, isothalic acid, napthalene dicarboxylic acid, together with aliphatic polymethylene glycols having 2 to 10 carbon atoms. Among these are ethylene glycol, trimethylene glycol, tetramethylene glycol, pentamethylene glycol, hexamethylene glycol, didecamethylene glycol and cyclohexane dimethanol.

Figure 2:
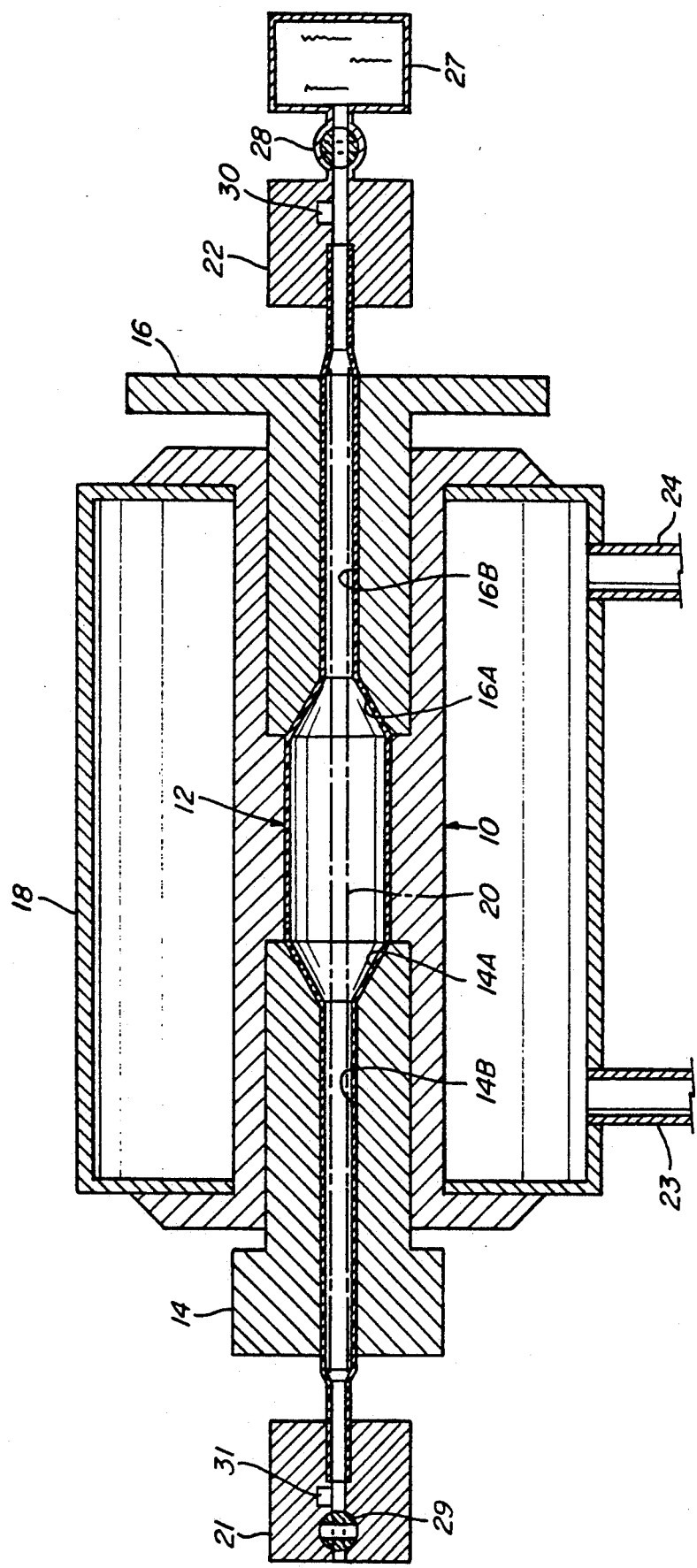
FIG. 2 is an illustration, in section of an alternative balloon forming mold having passages for circulating a heated fluid in the mold.

The PET parison is oriented at an elevated temperature, above the second order transition (orientation) temperature, as controlled by the heated fluid which flows through the parison. In an alternative embodiment shown in FIG. 2, in addition to providing a heated fluid through the parison, an the outer mold jacket 18 is provided with fluid passages 23, 24 for circulating a heated transfer fluid, such as hot water, to heat the outer surface of the parison to a lower temperature than the heated fluid which contacts the inner surface of the parison.

The orientation of the PET parison takes place at a temperature between the first and second order transition temperatures of the material, preferably from about 80° C. to 120° C., and more preferably at about 90° C. The parison is axially drawn from a starting length $L_1$ to a drawn length $L_2$. As shown in FIG. 3, the parison is circumferentially expanded from an initial internal diameter $ID_1$ and initial outer diameter $OD_1$ to a final internal diameter $ID_2$ and final outer diameter $OD_2$. The expanded balloon is then subjected to a heat set step in which steam is circulated through the outer mold at a temperature above the orientation or stretching temperature. Heat setting is done at a temperature between about 110° C. and 220° C., and preferably between about 130° C. and 170° C. The heat setting temperature is maintained for a fraction of a second or more, and preferably between about 5 to 30 seconds, sufficient to increase the degree of crystallinity in the balloon. The heat setting step is significant in assuring dimensional stability for the balloon, both during storage and also during inflation. After the heat set step, the balloon is then cooled to a temperature less than the second order transition temperature by flowing a cool fluid through the outer mold and/or a cool fluid through the parison. The balloon 12 thus formed may be removed from the mold by removing the end member 16 and withdrawing the formed balloon from the mold.

The relative amounts of stretch achieved at the inner and outer diameters is illustrated in FIG. 3. During circumferential expansion from parison 20 to balloon 12, the inner diameter stretch ratio $ID_2/ID_1$, is greater than the outer diameter stretch ratio $OD_2/OD_1$, because of the relative thicknesses of the parison and balloon—parison 20 being much thicker relative to balloon 12. In this invention, the temperature across the sidewall is varied to compensate for the higher stretch ratio at the inner diameter, namely by providing a linearly decreasing temperature gradient across the sidewall going from the inner to outer surfaces. The lower temperature at the outer surface thus produces more orientation from a given amount of stretch.

The use of a temperature gradient according to this invention enables one to produce a balloon having an average tensile strength of greater than 60% of the maximum potential tensile strength of the polymer. For PET, this would be a tensile strength of at least about 70 kpsi (thousand pounds per square inch). In further preferred embodiments the tensile strength is increased to at least about 90%, and more preferably 95% of the ultimate tensile strength.

The thin wall parison should have a wall thickness of no greater than about 25 mils. In further preferred embodiments the wall thickness would be no greater than about 20 mils, and more preferably no greater than about 15 mils.

The use of a temperature gradient is most beneficial where there is a substantial difference between the inner and outer diameter stretch ratios. Thus, for differences in stretch ratios of at least about 25%, and more preferably greater than 50%, the temperature gradient compensates for the difference and produces a substantially uniform amount of orientation across the sidewall. It has been observed that with the prior known methods of making balloons, the tensile strength at the outer diameter is at least 50% less than that at the inner diameter.

Preferably, in accordance with this invention, the difference in orientation across the sidewall of the balloon is no greater than about 50%, more preferably no greater than about 25%, and still further no greater than about 10%. The amount of average orientation across the sidewall can be estimated based on the increase in measured tensile strength or may be determinable directly by measuring the optical activity across the sidewall.

Although semi crystalline polymers such as PET are described herein as the preferred embodiment, other polymeric materials may be utilized with the temperature gradient method of this invention in order to increase the tensile strength of the balloon to a relatively high percentage of the maximum tensile strength of the given balloon material. Other suitable balloon materials may include polyurethane, nylon, polybutylene terephthalate (PBT), polyester and/or polyether block copolymers, ionomer resins, and combinations thereof. For example, a suitable polyester/polyether block copolymer may be that sold by E.I. Dupont de Nemours and Co., Wilmington, Del., under the trade name "Hytrel." Likewise, "Surlyn" is an ionomer resin sold by the same company.

In addition to increasing the average tensile strength, either the wall thickness can be decreased or burst strength may be increased, or a partial combination thereof (greater wall thickness corresponding to greater burst strength). In a preferred embodiment, the balloon has a wall thickness of no greater than about 4 mils (thousands of an inch), and more preferably no greater than about 1 mil. Alternatively, the burst strength can be increased to greater than 20 atm, and more preferably greater than 25 atm, without increasing the wall thickness.

The following theoretical examples illustrate the properties which may be achievable with the present invention as compared to a prior art balloon.

As a basis of comparison, a method of making a known balloon is described in the first column of Table 1. In this known process, a tubular parison is extruded from a high molecular weight PET homopolyester resin having an initial intrinsic viscosity in the range of 1.01 to 1.02, before extrusion. The intrinsic viscosity is slightly lowered during extrusion. The parison is heated in an external mold at a temperature of 91° C. for a period of about 1.13 minutes, on the assumption that the temperature across the entire sidewall of the parison will stabilize at 91° C. The parison is then stretched axially at the ratio of 3.3X, circumferentially at the inner diameter at 7.0X, and circumferentially at the outer diameter at 4.5X. The average circumferential stretch ratio is 5.5X, calculated by dividing the balloon outer diameter by the average diameter of the parison. The balloon is heat set at 150° C. for about ten seconds. The final balloon has an outer diameter of 4.0 mm and a wall thickness of 0.00889 mm.

The balloon has a measured burst strength of 18.2 atm. Burst pressure is determined by a simple laboratory procedure whereby one end of the polymeric balloon is sealed off and a pressurized gas is introduced incrementally into the other end. The inflation pressure at which the balloon bursts at about 37° C. (body temperature) is referred to herein as the burst pressure.

The average circumferential design tensile strength is calculated from the well known thin-walled pressure vessel equation:

$$S_c = PD/2t$$

where $S_c$ is the circumferential tensile strength, P is the burst pressure, D is the original (as molded) outer diameter of the balloon, and t is the wall thickness of the balloon (as molded). The calculated average circumferential tensile strength is 63.9 kpsi.

EXAMPLE 1

In a first theoretical example of the present invention, the goal is to optimize the average tensile strength by utilizing the known mold temperature (91° C.) and substituting the known ID stretch ratio (about 7.0X) for the OD stretch ratio. This will orient/strengthen the outside of the balloon to the strength of the strongest part of the known balloon. The inside of the balloon would be stretched much further, to about 14.1X, and the inside temperature would be raised above 91° C. to allow this higher stretch. The temperature of the ID would be ranged to find the temperature which produced the highest tensile strength. If the temperature is too low, the balloon will not form or the inner surface may be damaged. If the temperature is too high, the orientation would be less than optimum. This is an extreme process aimed at producing the ultimate tensile strength.

As shown in Table 1, it is estimated that a 56.5% increase in tensile strength can be achieved along with a 50.7% reduction in wall thickness. The burst strength is reduced 15.9%.

EXAMPLE 2

In a second example, a balloon is produced having the same wall thickness as the known product, but a higher average tensile strength. In this process, the ID stretch and temperature are kept the same as in the known process and the outer diameter (mold) temperature is lowered to increase the orientation/strength of the outer layers of the wall. The OD temperature would be ranged in order to equalize the orientation. The amount the OD temperature may be reduced is limited by the second order transmission temperature which may prevent achieving the optimum tensile strength.

As shown in Table 1, it is anticipated that a 56.5% increase in tensile strength may be achieved for the same wall thickness as the known example. In addition, a 70% increase in the burst strength may be achieved.

TABLE 1

|  | KNOWN | | EX. 1 | | EX. 2 | | EX. 3 | |
| --- | --- | --- | --- | --- | --- | --- | --- | --- |
|  | mm | inch | mm | inch | mm | inch | mm | inch |
| PARISON | | | | | | | | |
| ID | .584 | .023 | .279 | .011 | .584 | .023 | .432 | .017 |
| OD | .889 | .035 | .559 | .022 | .889 | .035 | .686 | .027 |
| AVG DIA | .737 | .029 | .432 | .017 | .737 | .029 | .559 | .022 |
| WALL | .152 | .006 | .127 | .005 | .152 | .006 | .127 | .005 |
| OUT TEMP. | 91° C. | | 91° C. | | <91° C. | | <91° C. | |
| INN TEMP. | est 91° C. | | >91° C. | | 91° C. | | >91° C. | |
| S AXIAL | 3.3 | | 3.3 | | 3.3 | | 3.3 | |
| S RAD ID | 7.0 | | 14.1 | | 7.0 | | 9.3 | |
| S RAD OD | 4.5 | | 7.2 | | 4.5 | | 5.9 | |
| S RAD AVG | 5.5 | | 9.5 | | 5.5 | | 7.2 | |
| BALLOON | | | | | | | | |
| OD | 4.0 | .1575 | 4.0 | .1575 | 4.0 | .1575 | 4.0 | .1575 |
| WALL | .00889 | .00035 | .0043815 | .0001725 | .00889 | .00035 | .00533 | .00021 |
| BURST (ATM) | 18.2 | | 15.3 | | 31.1 | | 18.3 | |
| AVG TENSL (KPSI) | 63.9 | | est 100 | | est 100 | | est 100 | |
| % REDUC WALL | NA | | 50.7 | | 0 | | 40 | |
| % INCRS TENSL | NA | | 56.5 | | 56.5 | | 56.5 | |
| % INCRS BURST | NA | | −15.9 | | 70.0 | | 0 | |

EXAMPLE 3

In a third embodiment, a "middle ground" approach is used in which the "average" diameter is stretched the same as the known ID stretch ratio with the ID at a temperature higher than the known process and the OD at a temperature lower than the known process. Thus, a higher average tensile strength would be achieved with a lower wall thickness.

As shown in Table 1, a 56.5% increase in tensile strength is estimated, along with a 40% reduction in wall thickness. The burst strength remains unchanged.

Balloons made at the various conditions set forth above can be burst at body temperature, and the tensile strength then calculated from the measured burst pressure. By plotting the various tensile strengths it is possible to locate the parameters necessary to achieve the maximum average tensile strength.

Having thus described the invention, what I claim and desire secure by letters patent is:

1. A method of making a thin wall dilatation balloon having a high percentage of the maximum tensile strength of the balloon material, the method comprising the steps of:
   heating a thin wall, tubular parison of a biaxially orientable polymer by flowing a heated fluid through the interior of the parison to achieve a radially decreasing temperature gradient across the sidewall of the parison going from the inner to the outer surface of the parison, the outer surface being heated to a temperature no less than the orientation temperature of the polymer and the parison having a wall thickness of no greater than about 25 mils;
   axially drawing and circumferentially expanding the parison while subject to said temperature gradient, said circumferential expansion being achieved by sealing one end of the parison and injecting a heated fluid to expand the parison; and
   wherein the temperature gradient is selected to compensate for differing degrees of stretch across the sidewall and produce the thin wall dilatation balloon having a substantially uniform and relatively high degree of orientation across the sidewall and thus a high average tensile strength.

2. The method of claim 1, wherein the temperature gradient is selected to produce a balloon having an average tensile strength greater than 60% of the maximum potential tensile strength of the polymer.

3. The method of claim 1, wherein the temperature gradient is selected to produce a balloon having a difference in orientation across the sidewall of less than 50%.

4. The method of claim 1, wherein the parison is axially drawn and circumferentially expanded to produce a balloon having a wall thickness of no greater than about 4 mils.

5. The method of claim 1, wherein the polymer is selected from the group consisting of polyester, polyurethane, nylon, polyester and/or polyether block copolymers, ionomer resins, and combinations thereof.

6. The method of claim 1, wherein the polymer is semi crystalline.

7. The method of claim 6, wherein the polymer is polyethylene terephthalate.

8. The method of claim 7, wherein the temperature gradient is selected to form a balloon having an average tensile strength of at least 70 kpsi.

9. A method of making a thin wall dilatation balloon having a high percentage of the maximum tensile strength of the balloon material, the method comprising the steps of:
   heating a thin wall, tubular parison of a biaxially orientable semi-crystalline polymer to achieve a radially decreasing temperature gradient across the sidewall of the parison going from the inner to the outer surfaces of the parison, the outer surface being heated to a temperature no less than the orientation temperature of the polymer, and the parison having a wall thickness of no greater than about 25 mils;
   axially drawing and circumferentially expanding the parison while subject to said temperature gradient, said circumferential expansion being achieved by sealing one end of the parison and injecting a heated fluid to expand the parison; and wherein the temperature gradient is selected to compensate for differing degrees of stretch across the sidewall and produce the thin wall dilatation balloon having a substantially uniform and relatively high degree of orientation across the sidewall and thus a high average tensile strength.

10. The method of claim 9, wherein the temperature qradient is selected to produce a balloon having an average tensile strength greater than 60% of the maximum potential tensile strength of the polymer.

11. The method of claim 9, wherein the temperature gradient is selected to produce a balloon having a difference in orientation across the sidewall of less than 50%.

12. The method of claim 9, wherein the parison is axially drawn and circumferentially expanded to produce a balloon having a wall thickness of no greater than about 4 mils.

13. The method of claim 9, wherein the polymer is polyethylene terephthalate.

14. A method of making a thin wall dilatation balloon from a tubular parison, wherein although the parison is expanded at substantially different inner and outer diameter stretch ratios, the resulting expanded article has a high percentage of the maximum tensile strength of the parison material, the method comprising the steps of:

heating a thin wall, tubular parison of a biaxially orientable polymer by flowing a heated fluid through the interior of the parison to achieve a radially decreasing temperature gradient across the sidewall of the parison going from the inner to the outer surfaces of the parison, the outer surface being heated to a temperature no less than the orientation temperature of the polymer and the parison having a wall thickness of no greater than about 25 mils;

axially drawing and circumferentially expanding the parison while subject to said temperature gradient, said circumferential expansion being achieved by sealing one end of the parison and injecting a heated fluid to expand the parison, and wherein the inner and outer diameter stretch ratios differ by at least about 25%; and wherein the temperature gradient across the sidewall is selected to compensate for the differing degrees of stretch across the sidewall and produce the thin wall dilation balloon having a substantially uniform and relatively high degree of orientation across the sidewall and thus a high average tensile strength.

15. The method of claim 14, wherein the temperature gradient is selected to produce a dilatation balloon having an average tensile strength of greater than 60% of the maximum potential tensile strength of the polymer.

16. The method of claim 14, wherein the temperature gradient is selected to produce a dilatation balloon having a difference in orientation across the sidewall of less than 50%.

17. The method of claim 14, wherein the parison is axially drawn and circumferentially expanded to produce a dilatation balloon having a wall thickness of no greater than about 4 mils.

18. The method of claim 14, wherein the polymer is selected from the group consisting of polyester, polyurethane, nylon, polyester and/or polyether block copolymers, ionomer resins, and combinations thereof.

19. The method of claim 17, wherein the polymer is polyethylene terephthalate.

20. A method of making a thin wall dilatation balloon having a high percentage of the maximum tensile strength of the balloon material, the method comprising the steps of:

heating a thin wall, tubular parison of a biaxially orientable, semi-crystalline polymer to achieve a radially decreasing temperature gradient across the sidewall of the parison going from the inner to the outer surfaces of the parison, the outer surface being heated to a temperature no less than the orientation temperature of the polymer and the parison having a wall thickness of no greater than about 25 mils;

axially drawing and circumferentially expanding the parison while subject to said temperature gradient, said circumferential expansion being achieved by sealing one end of the parison and injecting a heated fluid to expand the parison, and wherein the temperature gradient is selected to compensate for differing degrees of stretch across the sidewall to produce the thin wall dilatation balloon having a substantially unmiform and relatively high degree of orientation across the sidewall and thus a high average tensile strength, and heat setting the drawn and circumferentially expanded parison by elevating the temperature of the formed balloon and maintaining the temperature for a period of time sufficient for heat setting the balloon and ensuring the dimensional stability of the balloon.

21. The method of claim 20 wherein the semi-crystalline polymer is polyethylene terephthalate.

22. The method of claim 21 wherein the heat setting temperature is between about 110° C. and 220° C.

23. The method of claim 20, wherein the temperature gradient is selected to produce a balloon having an average tensile strength greater than 60% of the maximum potential tensile strength of the polymer.

24. The method of claim 20, wherein the temperature gradient is selected to produce a balloon having a difference in orientation across the sidewall of less than 50%.

25. The method of claim 20, wherein the parison is axially drawn and circumferentially expanded to produce a balloon having a wall thickness of no greater than about 4 mils.

* * * * *